United States Patent
Dwork et al.

(10) Patent No.: US 8,876,893 B2
(45) Date of Patent: Nov. 4, 2014

(54) TRANSCATHETER PROSTHETIC HEART VALVE DELIVERY DEVICE WITH PASSIVE TRIGGER RELEASE

(75) Inventors: Joshua Dwork, Santa Rosa, CA (US); Glenn Stante, Turlock, CA (US); Adam Shipley, San Rafael, CA (US)

(73) Assignee: Medtronic, Inc., Minneapolis, MN (US)

( * ) Notice: Subject to any disclaimer, the term of this patent is extended or adjusted under 35 U.S.C. 154(b) by 844 days.

(21) Appl. No.: 13/095,147

(22) Filed: Apr. 27, 2011

(65) Prior Publication Data

US 2011/0264203 A1  Oct. 27, 2011

Related U.S. Application Data

(60) Provisional application No. 61/328,230, filed on Apr. 27, 2010.

(51) Int. Cl.
*A61F 2/24* (2006.01)

(52) U.S. Cl.
USPC ........... 623/2.11; 606/191; 606/192; 606/194

(58) Field of Classification Search
USPC .......... 606/191, 192, 194, 195, 198; 623/2.11
See application file for complete search history.

(56) References Cited

U.S. PATENT DOCUMENTS

| | | | |
|---|---|---|---|
| 5,683,451 A | | 11/1997 | Lenker et al. |
| 5,824,041 A | | 10/1998 | Lenker et al. |
| 5,906,619 A | | 5/1999 | Olson et al. |
| 5,957,949 A | | 9/1999 | Leonhardt et al. |
| 6,858,034 B1 * | 2/2005 | Hijlkema et al. ............. 606/108 |
| 8,465,541 B2 * | 6/2013 | Dwork .......................... 623/2.11 |
| 8,512,400 B2 * | 8/2013 | Tran et al. ..................... 623/2.11 |
| 8,512,401 B2 * | 8/2013 | Murray et al. ................ 623/2.11 |
| 2003/0199963 A1 | 10/2003 | Tower et al. |
| 2005/0137688 A1 | 6/2005 | Salahieh et al. |
| 2006/0004439 A1 | 1/2006 | Spenser et al. |
| 2006/0052867 A1 | 3/2006 | Revuelta et al. |
| 2006/0259136 A1 | 11/2006 | Nguyen et al. |
| 2006/0265056 A1 | 11/2006 | Nguyen et al. |
| 2007/0005131 A1 | 1/2007 | Taylor |
| 2007/0088431 A1 | 4/2007 | Bourang et al. |
| 2007/0239266 A1 | 10/2007 | Birdsall |
| 2007/0239269 A1 | 10/2007 | Dolan et al. |
| 2008/0065011 A1 | 3/2008 | Marchand et al. |

(Continued)

FOREIGN PATENT DOCUMENTS

| | | |
|---|---|---|
| GB | 2433700 | 7/2007 |
| WO | WO00/71059 | 11/2000 |

(Continued)

*Primary Examiner* — Vy Q Bui

(57) ABSTRACT

A delivery device for percutaneously deploying a prosthetic valve includes a sheath, an inner shaft, and a release assembly. The release assembly is disposed between the sheath and the inner shaft, and includes a retraction member, a release member, and a retention member. The retraction member can self-retract in length from an extended condition to a retracted condition. The release member can self-expand from a compressed condition to an expanded condition. The retention member is distal the release member. In a delivery state, the sheath end is distal the retention member, the release member is in the compressed condition and the retraction member in the extended condition to retain the prosthesis. In a deployment state, the sheath end is positioned to permit the release member to self-transition to the expanded condition, allowing the retraction member to self-transition to the retracted condition and release the prosthesis.

26 Claims, 12 Drawing Sheets

(56) References Cited

U.S. PATENT DOCUMENTS

| | | |
|---|---|---|
| 2008/0082165 A1 | 4/2008 | Wilson et al. |
| 2008/0147160 A1 | 6/2008 | Ghione et al. |
| 2008/0147181 A1 | 6/2008 | Ghione et al. |
| 2008/0188928 A1 | 8/2008 | Salahieh et al. |
| 2008/0234797 A1 | 9/2008 | Styrc |
| 2008/0255651 A1 | 10/2008 | Dwork |
| 2009/0093876 A1 | 4/2009 | Nitzan et al. |
| 2009/0138079 A1 | 5/2009 | Tuval et al. |
| 2009/0171447 A1 | 7/2009 | Von Segesser et al. |
| 2009/0177275 A1 | 7/2009 | Case |
| 2009/0281619 A1 | 11/2009 | Le et al. |
| 2010/0049313 A1 | 2/2010 | Alon et al. |
| 2010/0094411 A1 | 4/2010 | Tuval et al. |
| 2010/0121434 A1 | 5/2010 | Paul et al. |

FOREIGN PATENT DOCUMENTS

| | | |
|---|---|---|
| WO | 2008/138584 | 11/2008 |
| WO | 2009/091509 | 7/2009 |
| WO | WO2011/025945 | 3/2011 |

* cited by examiner

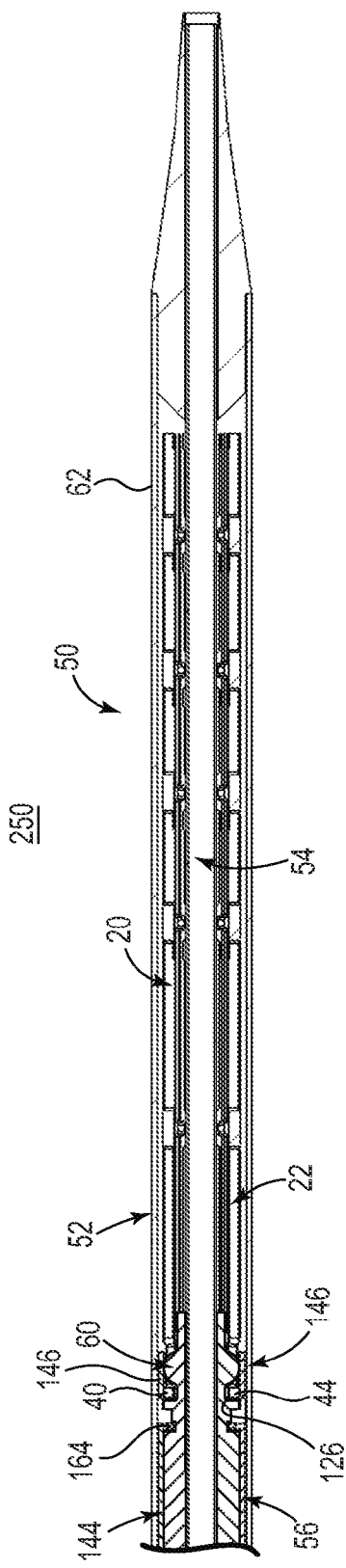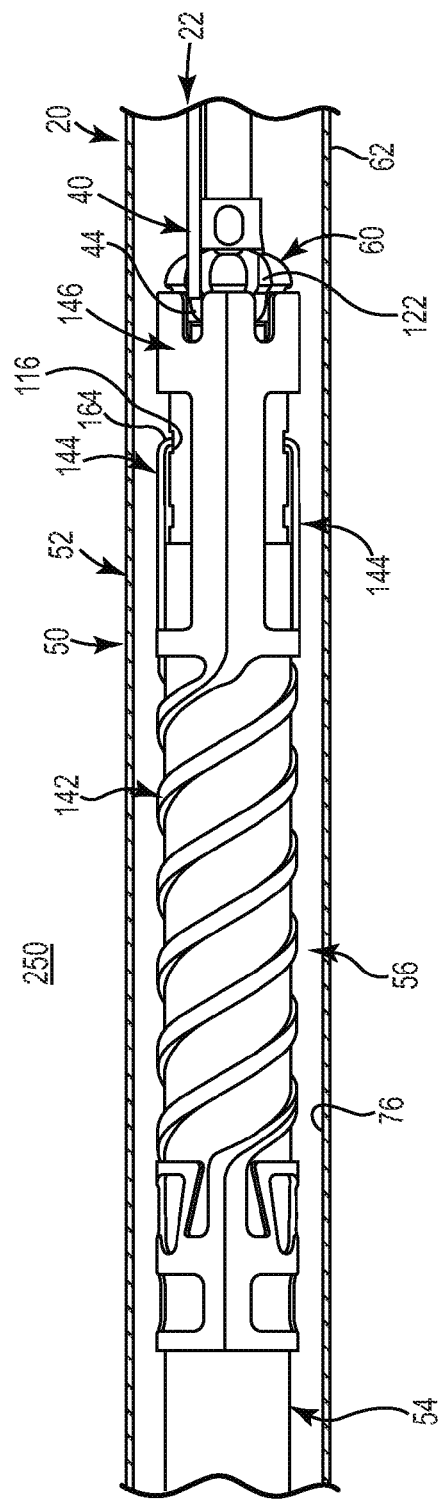

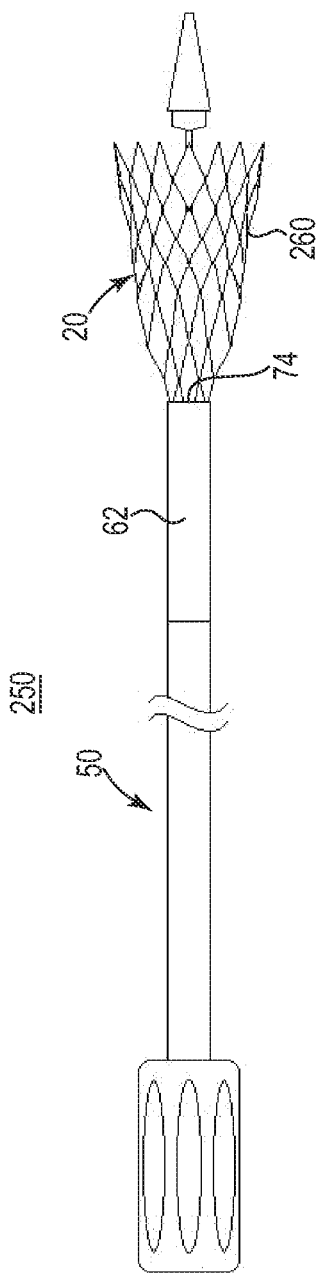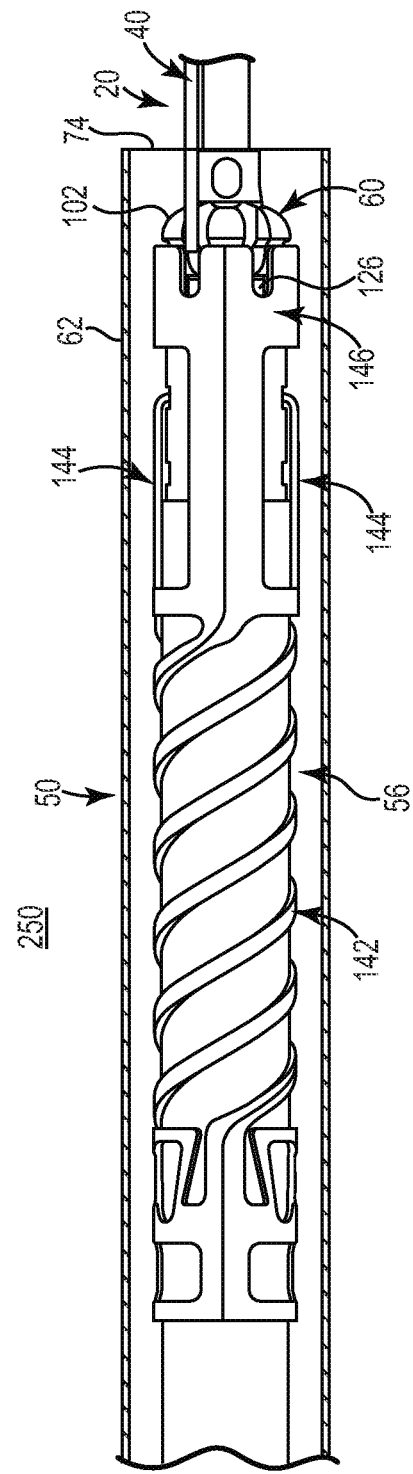

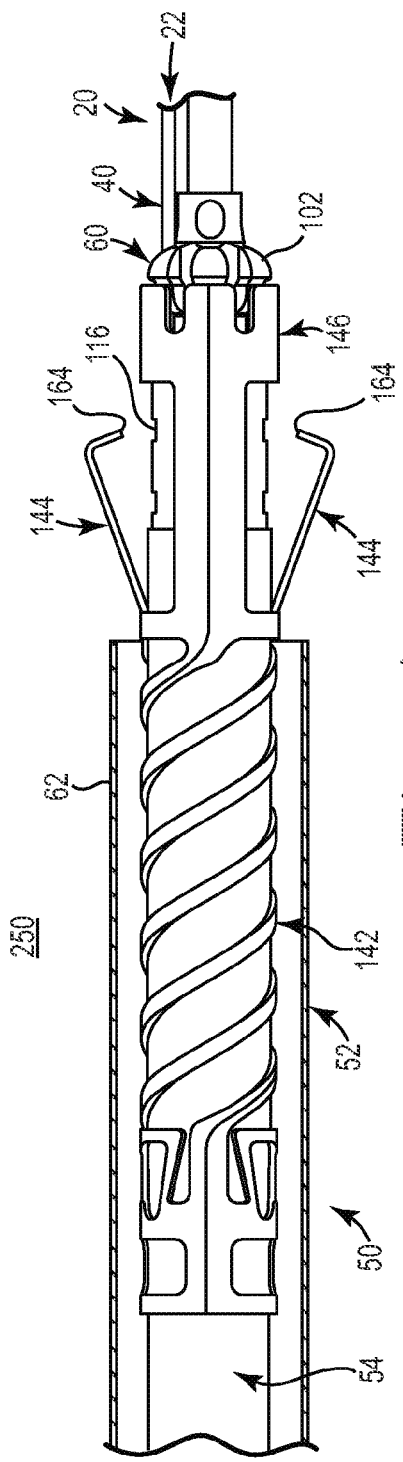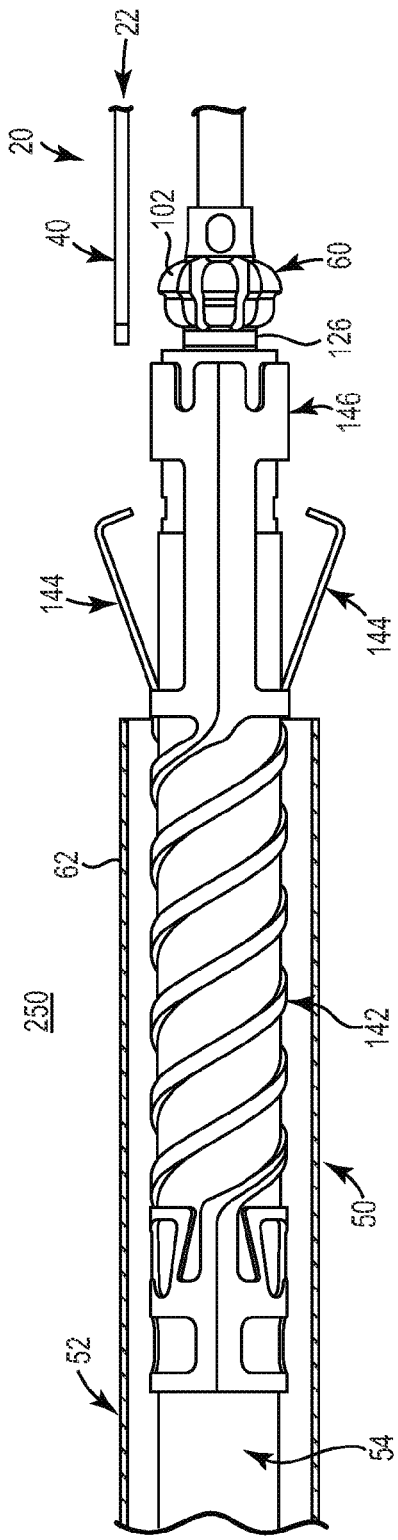

TRANSCATHETER PROSTHETIC HEART VALVE DELIVERY DEVICE WITH PASSIVE TRIGGER RELEASE

CROSS-REFERENCE TO RELATED APPLICATIONS

This application claims priority under 35 U.S.C. §119(e)(1) to U.S. Provisional Patent Application Ser. No. 61/328,230, filed Apr. 27, 2010, entitled "Transcatheter Prosthetic Heart Valve Delivery Device with Passive Trigger Release"; the entire teachings of which are incorporated herein by reference.

BACKGROUND

The present disclosure relates to systems, devices, and methods for percutaneous implantation of a prosthetic heart valve. More particularly, it relates to delivery systems, devices, and methods for transcatheter implantation of a stented prosthetic heart valve.

Diseased or otherwise deficient heart valves can be restored, repaired or replaced with an implanted prosthetic heart valve. The terms "repair," "restore," and "replace" are used interchangeably throughout this specification, and reference to "restoring" a defective heart valve is inclusive of implanting a prosthetic heart valve that renders the native leaflets non-functional, or that leaves the native leaflets intact and functional. Conventionally, heart valve replacement surgery is an open-heart procedure conducted under general anesthesia, during which the heart is stopped and blood flow is controlled by a heart-lung bypass machine. Traditional open surgery inflicts significant patient trauma and discomfort, and exposes the patient to a number of potential risks, such as infection, stroke, renal failure, and adverse effects associated with the use of the heart-lung bypass machine, for example.

Due to the drawbacks of open-heart surgical procedures, there has been an increased interest in minimally invasive and percutaneous replacement of cardiac valves. With percutaneous transcatheter (or transluminal) techniques, a valve prosthesis is compacted for delivery in a catheter and then advanced, for example, through an opening in the femoral artery and through the descending aorta to the heart, where the prosthesis is then deployed in the annulus of the valve to be restored (e.g., the aortic valve annulus). Although transcatheter techniques have attained widespread acceptance with respect to the delivery of conventional stents to restore vessel patency, only mixed results have been realized with percutaneous delivery and implantation of the more complex prosthetic heart valve.

Various types and configurations of prosthetic heart valves are available for percutaneous valve replacement procedures, and continue to be refined. The actual shape and configuration of any particular transcatheter prosthetic heart valve is dependent to some extent upon the native shape and size of the valve being replaced (i.e., mitral valve, tricuspid valve, aortic valve, or pulmonary valve). In general, prosthetic heart valve designs attempt to replicate the functions of the valve being replaced and thus will include valve leaflet-like structures. With a bioprostheses construction, the replacement valve may include a valved vein segment that is mounted in some manner within an expandable stent frame to make a valved stent (or "stented prosthetic heart valve"). For many percutaneous delivery and implantation devices, the stent frame of the valved stent is made of a self-expanding material and construction. With these devices, the valved stent is crimped down to a desired size and held in that compressed arrangement within an outer delivery sheath, for example. Retracting the sheath from the valved stent allows the stent to self-expand to a larger diameter, such as when the valved stent is in a desired position within a patient. In other percutaneous implantation devices, the valved stent can be initially provided in an expanded or uncrimped condition, then crimped or compressed on a balloon portion of catheter until it is as close to the diameter of the catheter as possible. The so-loaded balloon catheter is slidably disposed within an outer delivery sheath. Once delivered to the implantation site, the balloon is inflated to deploy the prosthesis. With either of these types of percutaneous stented prosthetic valve delivery techniques, conventional sewing of the prosthetic heart valve to the patient's native tissue is typically not necessary.

It is imperative that the stented prosthetic heart valve be accurately located relative to the native annulus immediately prior to full deployment from the catheter as successful implantation requires the prosthetic heart valve intimately lodge and seal against the native annulus. If the prosthesis is incorrectly positioned relative to the native annulus, serious complications can result as the deployed device can leak and may even dislodge from the native valve implantation site. As a point of reference, this same concern does not arise in the context of vascular stents; with these procedures, if the target site is "missed," another stent is simply deployed to "make-up" the difference.

To carefully and safely deploy a transcatheter prosthetic heart valve, a clinician can employ imaging technology to evaluate the location of the prosthesis immediately prior to deployment. Along these lines, one desirable transcatheter prosthetic heart valve implantation technique entails partially deploying a distal region of the prosthesis from the delivery device and then evaluating a position of the deployed distal region relative to the native annulus. The clinician may further desire the ability to resheath or recapture the partially deployed region for subsequent repositioning of the prosthesis. Regardless, in the partially deployed state, the proximal region of the prosthetic heart valve must remain coupled to the delivery device. While, in theory, retaining a partially deployed prosthetic heart valve to the delivery device is straightforward, in actual practice the constraints presented by the stented prosthetic heart valve render the technique exceedingly difficult. In particular, the delivery device must not only securely retain the prosthetic heart valve in the partially deployed state, but also must consistently operate to release the prosthetic heart valve when full deployment is desired.

A stented heart valve is purposefully designed to rigidly resist collapsing forces once deployed so as to properly anchor itself in the anatomy of the heart. Thus, the delivery device component (e.g., outer delivery sheath) employed to retain the prosthesis in a collapsed arrangement must be capable of exerting a significant radial force. Conversely, this same component cannot be overly rigid so as to avoid damaging the transcatheter heart valve during deployment. Further, the aortic arch must be traversed with many percutaneous heart valve replacement procedures, necessitating that the delivery device provide sufficient articulation attributes. To meet these constraints, the outer delivery sheath typically incorporates a circumferentially rigid capsule, and a coupling structure is disposed within the delivery sheath for temporarily capturing the stented valve. While viable, conventional delivery device designs robustly engage the prosthetic heart valve within the capsule; this robust engagement facilitates the partial deployment technique described above, but the prosthetic heart valve may undesirably catch on the inner engagement structure when full deployment is intended and/or numerous, complex components are required to ensure complete deployment. Further, clinicians prefer that a significant portion of the prosthetic heart valve be exposed/expanded in the partially deployed state (e.g., the inflow region and at least a portion of the outflow region of the prosthesis). Unfortunately, existing delivery device designs cannot consistently meet this preference.

In light of the above, a need exists for heart valve replacement systems and corresponding stented transcatheter prosthetic heart valve delivery devices and methods that satisfy the constraints associated with percutaneous heart valve implantation and permit consistent partial and full deployment of the prosthesis.

SUMMARY

Some aspects in accordance with principles of the present disclosure relate to a delivery device for percutaneously deploying a stented prosthetic heart valve. The prosthetic heart valve has a stent frame to which a valve structure is attached. The delivery device includes a delivery sheath, an inner shaft assembly, and a release assembly. The delivery sheath terminates at a distal end and defines a lumen. The inner shaft assembly is slidably disposed within the lumen and includes an engagement structure configured to selectively engage a prosthetic heart valve. The release assembly is disposed between the delivery sheath and the inner shaft assembly, and defines a central longitudinal axis. Further, the release assembly includes a base, a retraction member, a release member, and a retention member. The base is coupled to the inner shaft assembly proximal the engagement structure. The retraction member extends distal the base and is configured to self-retract in longitudinal length from an expanded condition to a normal, retracted condition. The release member extends distal the retraction member, and is configured to self-expand in radial projection relative to the central axis from a compressed condition to a normal, expanded condition. Finally, the retention member is located distal the release member. With this construction, the device is configured to provide a delivery state and a deployment state. In the delivery state, the distal end of the delivery sheath is distal the retention member, with the release member in the compressed condition and the retraction member in the extended condition. In the deployment state, the distal end of the delivery sheath is proximal the release member, permitting the release member to self-transition to the normal, expanded condition. Further, the retraction member is permitted to self-transition to the normal, retracted condition. Thus, the release assembly effectively "senses" proximal retraction of the delivery sheath via self-transitioning of the release member, and, in turn, causes the retraction member to move proximally (via allowed firing of the retraction member) to effectuate release of a loaded prosthetic heart valve. In some embodiments, the retention member is a linear spring, such as a spiral-cut metal tube. In other embodiments, the release member is a deflection arm having a fixed end, a free end, and an intermediate portion imparted with a memory set curved shape. In related embodiments, the inner shaft assembly forms a notch sized to receive the free end in the compressed condition of the release member. In yet other embodiments, two release member deflection arms are provided with the release assembly.

Yet other aspects in accordance with principles of the present disclosure relate to a system for restoring (e.g., replacing) a defective heart valve of a patient. The system includes a prosthetic heart valve and the delivery device as described above. The prosthetic heart valve has a stent frame and a valve structure attached to the stent frame. Further, the stent frame includes a proximal region forming at least one post. In a loaded mode of the system, the prosthetic heart valve is contained between the delivery sheath and the inner shaft assembly. Further, the retraction member is forced to the extended condition to position the retention member over the engagement structure, with the post being slidably coupled to the engagement structure via the retention member. In a deployment mode of the system, the delivery sheath is proximally withdrawn from the prosthetic heart valve and the release member, permitting the release member to self-transition to the expanded condition and the retraction member to self-retract to the retracted condition. As a result, the retention member is withdrawn from over the post to permit the prosthetic heart valve to deploy from the inner shaft assembly. In some embodiments, the delivery device is further transitionable from the deployment mode to a removal state following deployment of the prosthetic heart valve, the removal state including the distal end of the delivery sheath being distal the release member to force the release member to the compressed condition and the retraction member maintaining the retracted condition. In the removal state, then, the delivery device assumes a low profile for ready removal from the patient.

Yet other aspects in accordance with principles of the present disclosure relate to a method of percutaneously deploying a stented prosthetic heart valve to an implantation site. The method includes receiving a delivery device loaded with a radially expandable prosthetic heart valve having a stent frame to which a valve structure is attached. The delivery device includes a delivery sheath containing the prosthetic heart valve in a compressed arrangement over an inner shaft assembly in a delivery state of the device. Further, the delivery device includes a release assembly having a base, a retraction member, a release member, and a retention member. The base is coupled to the inner shaft assembly. The retraction member extends distal the base and is forced to an extended condition. The release member extends distal the retraction member and is forced to a compressed arrangement in which the release member engages the inner shaft assembly to retain the retraction member in the extended condition. The retention member extends distal the release member and is disposed over a post of the prosthetic heart valve. The prosthetic heart valve is delivered in the compressed arrangement through a bodily lumen of a patient and to the implantation site via the delivery device in the delivery state. The delivery sheath is proximally retracted from the prosthetic heart valve and the retention member. The post is permitted to release from the engagement structure including the release member self-transitioning to a normal, expanded condition and the retraction member self-retracting to a relaxed, retracted condition to proximally withdraw the retention member from the post. With this technique, the separate release and retraction members independently provide sheath sensing and retraction functions, minimizing possible malfunctions of the release assembly.

BRIEF DESCRIPTION OF THE DRAWINGS

FIG. 7A is an enlarged, cross-sectional view of a portion of a heart valve repair or replacement system in accordance with principles of the present disclosure, including the delivery device of FIG. 3 loaded with the prosthetic heart valve of FIG. 1A;

FIG. 7B is an enlarged, side view of a portion of the system of FIG. 7A;

FIG. 8A is a simplified side view of the system of FIG. 7A in an initial stage of a deployment mode;

FIG. 8B is an enlarged, side view of a portion of the system of FIG. 8A, including portions shown in cross-section;

FIGS. 9A and 9B are simplified perspective views of the delivery device of FIG. 3 in various stages of transitioning to a deployment state.

DETAILED DESCRIPTION

Figure 1A:
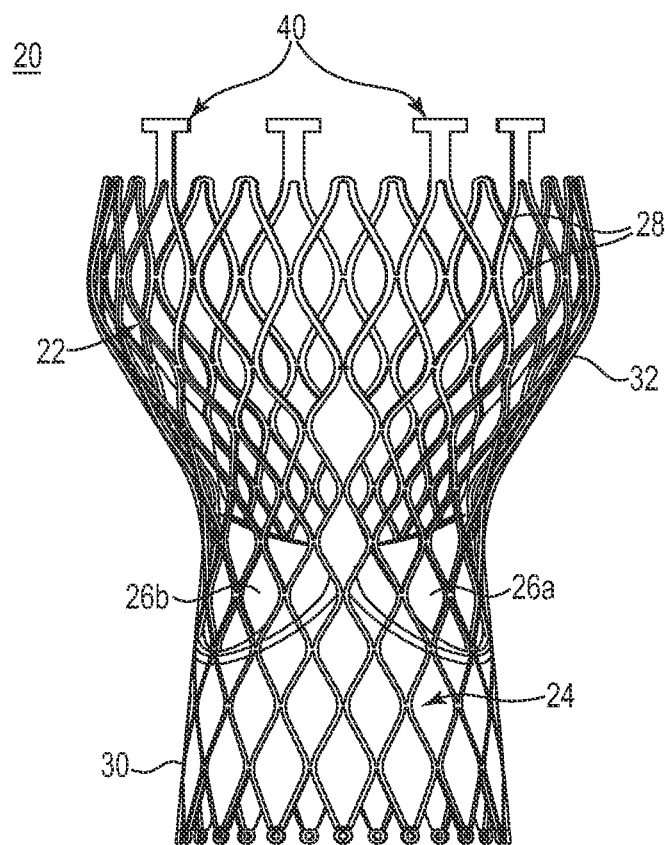
FIG. 1A is a side view of a stented prosthetic heart valve useful with systems, devices, and methods of the present disclosure and in a normal, expanded arrangement.

As referred to herein, stented transcatheter prosthetic heart valves useful with and/or as part of the various systems, devices, and methods of the present disclosure may assume a wide variety of different configurations, such as a bioprosthetic heart valve having tissue leaflets or a synthetic heart valve having polymeric, metallic, or tissue-engineered leaflets, and can be specifically configured for replacing any heart valve. Thus, the stented prosthetic heart valve useful with the systems, devices, and methods of the present disclosure can be generally used for replacement of a native aortic, mitral, pulmonic, or tricuspid valve, for use as a venous valve, or to replace or restore a failed bioprosthesis, such as in the area of an aortic valve or mitral valve, for example.

In general terms, the stented prosthetic heart valves of the present disclosure include a stent or stent frame maintaining a valve structure (tissue or synthetic), with the stent having a normal, expanded arrangement and collapsible to a compressed arrangement for loading within a delivery device. The stent is normally constructed to self-deploy or self-expand when released from the delivery device. For example, the stented prosthetic heart valve useful with the present disclosure can be a prosthetic valve sold under the trade name CoreValve® available from Medtronic CoreValve, LLC. Other non-limiting examples of transcatheter heart valve prostheses useful with systems, devices, and methods of the present disclosure are described in U.S. Publication Nos. 2006/0265056; 2007/0239266; and 2007/0239269, the teachings of each which are incorporated herein by reference. The stents or stent frames are support structures that comprise a number of struts or wire portions arranged relative to each other to provide a desired compressibility and strength to the prosthetic heart valve. In general terms, the stents or stent frames of the present disclosure are generally tubular support structures having an internal area in which valve structure leaflets will be secured. The leaflets can be formed from a variety of materials, such as autologous tissue, xenograph material, or synthetics as are known in the art. The leaflets may be provided as a homogenous, biological valve structure, such as porcine, bovine, or equine valves. Alternatively, the leaflets can be provided independent of one another (e.g., bovine or equine paracardial leaflets) and subsequently assembled to the support structure of the stent frame. In another alternative, the stent frame and leaflets can be fabricated at the same time, such as may be accomplished using high-strength nano-manufactured NiTi films produced at Advance BioProsthetic Surfaces (ABPS), for example. The stent frame support structures are generally configured to accommodate at least two (typically three) leaflets; however, replacement prosthetic heart valves of the types described herein can incorporate more or less than three leaflets.

Some embodiments of the stent frames can be a series of wires or wire segments arranged such that they are capable of self-transitioning from a compressed or collapsed arrangement to the normal, radially expanded arrangement. In some constructions, a number of individual wires comprising the stent frame support structure can be formed of a metal or other material. These wires are arranged in such a way that the stent frame support structure allows for folding or compressing or crimping to the compressed arrangement in which the internal diameter is smaller than the internal diameter when in the normal, expanded arrangement. In the compressed arrangement, such a stent frame support structure with attached valve leaflets can be mounted onto a delivery device. The stent frame support structures are configured so that they can be changed to their normal, expanded arrangement when desired, such as by the relative movement of one or more sheaths relative to a length of the stent frame.

The wires of these stent frame support structures in embodiments of the present disclosure can be formed from a shape memory material such as a nickel titanium alloy (e.g., Nitinol™). With this material, the support structure is self-expandable from the compressed arrangement to the normal, expanded arrangement, such as by the application of heat, energy, and the like, or by the removal of external forces (e.g., compressive forces). This stent frame support structure can also be compressed and re-expanded multiple times without damaging the structure of the stent frame. In addition, the stent frame support structure of such an embodiment may be laser-cut from a single piece of material or may be assembled from a number of different components. For these types of stent frame structures, one example of a delivery device that can be used includes a catheter with a retractable sheath that covers the stent frame until it is to be deployed, at which point the sheath can be retracted to allow the stent frame to self-expand. Further details of such embodiments are discussed below.

Figure 1B:
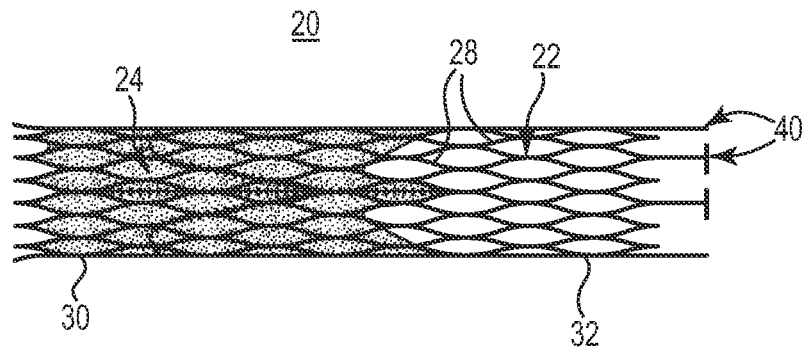
FIG. 1B is a side view of the prosthetic heart valve of FIG. 1A in a compressed arrangement.

With the above understanding in mind, one non-limiting example of a stented prosthetic heart valve 20 useful with systems, devices, and methods of the present disclosure is illustrated in FIGS. 1A and 1B. As a point of reference, the prosthetic heart valve 20 is shown in a normal or expanded arrangement in the view of FIG. 1A; FIG. 1B illustrates the prosthetic heart valve 20 in a compressed arrangement (e.g., when compressively retained within an outer catheter or sheath). The prosthetic heart valve 20 includes a stent or stent frame 22 and a valve structure 24. The stent frame 22 can assume any of the forms described above, and is generally constructed so as to be self-expandable from the compressed arrangement (FIG. 1B) to the normal, expanded arrangement (FIG. 1A). In other embodiments, the stent frame 22 is expandable to the expanded arrangement by a separate device (e.g., a balloon internally located within the stent frame 22). The valve structure 24 is assembled to the stent frame 22 and provides two or more (typically three) leaflets 26a, 26b. The valve structure 24 can assume any of the forms described above, and can be assembled to the stent frame 22 in various manners, such as by sewing the valve structure 24 to one or more of the wire segments 28 defined by the stent frame 22.

With the but one acceptable construction of FIGS. 1A and 1B, the prosthetic heart valve 20 is configured for restoring an aortic valve. Alternatively, other shapes are also envisioned, adapted for the specific anatomy of the valve to be replaced (e.g., stented prosthetic heart valves in accordance with the present disclosure can alternatively be shaped and/or sized for replacing a native mitral, pulmonic, or tricuspid valve). Regardless, the valve structure 24 can be arranged to extend less than an entire length of the stent frame 22. In particular, the valve structure 24 can be assembled to, and extend along, an inflow region 30 of the prosthetic heart valve 20, whereas an outflow region 32 is free of the valve structure 24 material. The terms "inflow" and "outflow" are in reference to an arrangement of the prosthetic heart valve 20 upon final implantation relative to the native aortic valve (or other valve) being repaired. A wide variety of other constructions are also acceptable and within the scope of the present disclosure. For example, the valve structure 24 can be sized and shaped to extend along an entirety, or a near entirety, of a length of the stent frame 22. With embodiments in which the prosthetic heart valve 20 is to be implanted via a retrograde approach, the prosthetic heart valve 20 will be arranged within the corresponding delivery device such that the inflow region 30 is distal the outflow region 32. Thus, the inflow region 30 can alternatively be referenced as the distal region of the prosthetic heart valve 20, whereas the outflow region 32 serves as the proximal region. With these conventions in mind, a proximal end 36 of the stent frame 22 forms, in some embodiments, a plurality of posts 40. The posts 40 are defined at an intersection of two (or more) adjacent ones of the wire segments 28, and are circumferentially spaced about a circumference defined by the stent frame 22. While the stent frame 22 is shown in FIGS. 1A and 1B as having four of the posts 40, any other number, either greater or lesser, is equally acceptable. For example, the stent frame 22 can include as few as a single one of the posts 40.

Figure 2:
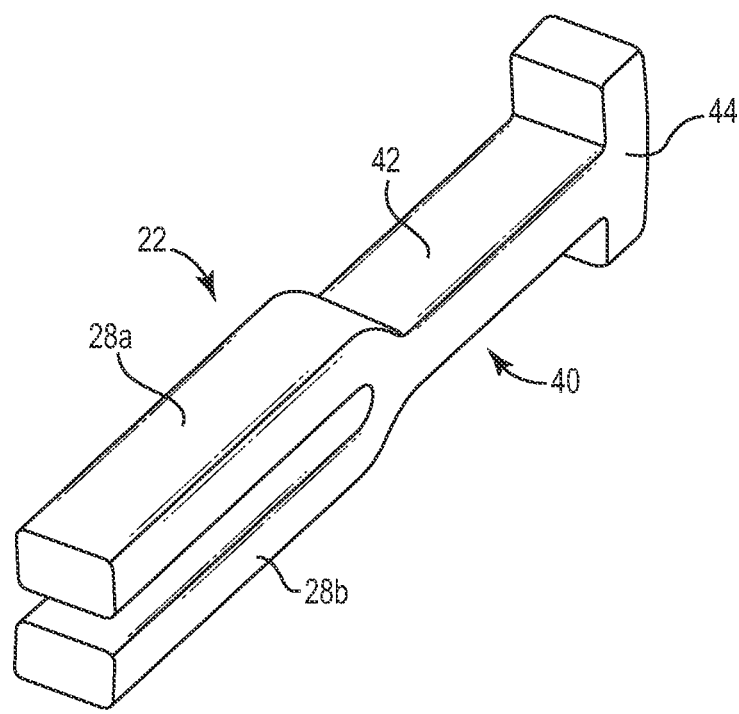
FIG. 2 is an enlarged, perspective view of a post portion of the prosthetic heart valve of FIGS. 1A and 1B.

The posts 40 can assume various forms, and in some embodiments are identical. FIG. 2 illustrates one construction of the post 40 contemplated by the present disclosure in greater detail. As a point of reference, in the view of FIG. 2, two of the wire segments 28a, 28b are illustrated as intersecting at the post 40, with the post 40 projecting proximally from the wire segments 28a, 28b; a remainder of the stent frame 22 is omitted from the view for ease of explanation. The post 40 includes a shoulder 42 and a head 44. With respect to an orientation of the post 40 relative to the circumference defined by the stent frame 22 (FIG. 1A), the shoulder 42 and the head 44 can be described as having or defining a circumferential width, with the circumferential width of the head 44 being greater than that of the shoulder 42 for reasons made clear below. With some constructions, then, the post 40 can have a T-like shape. Other shapes are also acceptable. These and other features of the post 40, as well as the stent frame 22 as a whole, are described below in the context of loading to, and releasing from, a delivery device.

Figure 3:
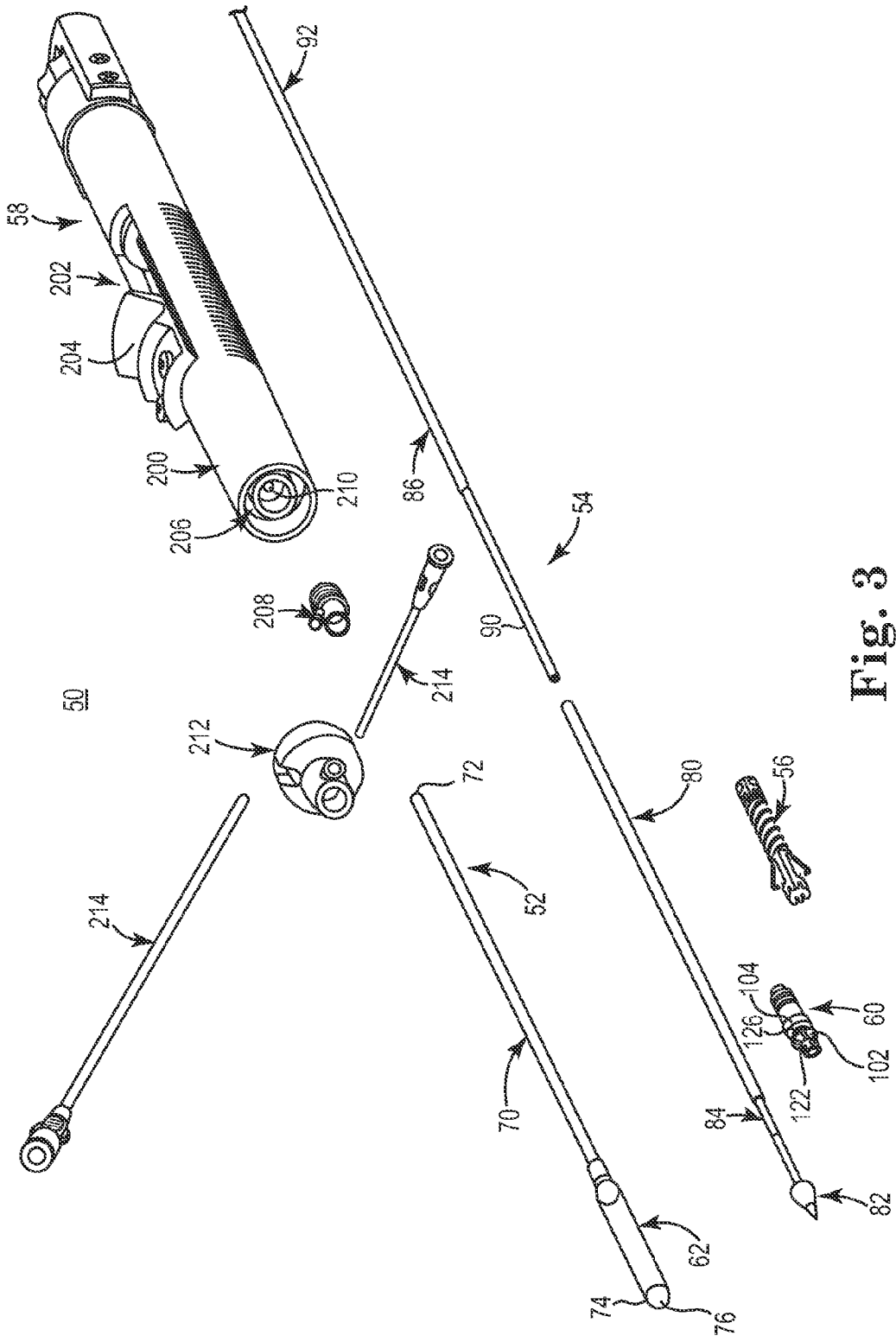
FIG. 3 is an exploded, perspective view of a stented prosthetic heart valve delivery device in accordance with principles of the present disclosure.

With the above understanding of the prosthetic heart valve 20 in mind, one embodiment of a transcatheter stented prosthetic heart valve delivery device 50 in accordance with principles of the present disclosure is shown in FIG. 3. The delivery device 50 includes a delivery sheath assembly 52, an inner shaft assembly 54, a release assembly 56, and a handle 58. Details on the various components are provided below. In general terms, however, the delivery device 50 combines with a stented prosthetic heart valve (not shown) to form a system for restoring (e.g., replacing) a defective heart valve of a patient. The delivery device 50 provides a delivery or loaded state in which a stented prosthetic heart valve is coupled to the inner shaft assembly 54 (e.g., a spindle 60 component of the inner shaft assembly 54), and compressively retained within a capsule 62 of the delivery sheath assembly 52. In this regard, the release assembly 56 robustly retains the stented prosthetic heart valve relative to the inner shaft assembly 54. The delivery sheath assembly 52 can be manipulated to withdraw the capsule 62 from the prosthetic heart valve via operation of the handle 58, permitting the prosthesis to self-expand and release from the inner shaft assembly 54. More particularly, the release assembly 56 self-retracts from the prosthetic heart valve in response to proximal retraction of the capsule 62. The release assembly 56 thus serves as a passive trigger for the delivery device 50 with self-actuation of the release assembly 56 being dictated by a location of the capsule 62 relative thereto. Further, in some embodiments, the handle 58 can be operated to maneuver the capsule 62 to effectuate a partial deployment state in which a distal region of the prosthetic heart valve is permitted to self-expand, whereas a proximal region of the prosthesis remains coupled to the inner shaft assembly 54 via the release assembly 56.

Various features of the components 52-60 reflected in FIG. 3 and described below can be modified or replaced with differing structures and/or mechanisms. Thus, the present disclosure is in no way limited to the delivery sheath assembly 52, the inner shaft assembly 54, the handle 58, etc., as shown and described below. More generally, delivery devices in accordance with the present disclosure provide features (e.g., the capsule 62 in combination with the release assembly 56) capable of compressively retaining a self-deploying, stented prosthetic heart valve, and a mechanism capable of consistently releasing the prosthesis with retraction of the capsule 62 (e.g., the release assembly 56).

In some embodiments, the delivery sheath assembly 52 includes the capsule 62 and a shaft 70, and defines proximal and distal ends 72, 74. A lumen 76 is formed by the delivery sheath assembly 52, extending from the distal end 74 through the capsule 62 and at least a portion of the shaft 70. The lumen 76 can be open at the proximal end 72. The capsule 62 extends distally from the shaft 70, and in some embodiments has a more stiffened construction (as compared to a stiffness of the shaft 70) that exhibits sufficient radial or circumferential rigidity to overtly resist the expected expansive forces of the stented prosthetic heart valve (not shown) when compressed within the capsule 62. For example, the shaft 70 can be a polymer tube embedded with a metal braiding, whereas the capsule 62 includes a laser-cut metal tube that is optionally embedded within a polymer covering. Alternatively, the capsule 62 and the shaft 70 can have a more uniform construction (e.g., a continuous polymer tube). Regardless, the capsule 62 is constructed to compressively retain the stented prosthetic heart valve at a predetermined diameter when loaded within the capsule 62, and the shaft 70 serves to connect the capsule 62 with the handle 58. The shaft 70 (as well as the capsule 62) is constructed to be sufficiently flexible for passage through a patient's vasculature, yet exhibits sufficient longitudinal rigidity to effectuate desired axial movement of the capsule 62. In other words, proximal retraction of the shaft 70 is directly transferred to the capsule 62 and causes a corresponding proximal retraction of the capsule 62. In other embodiments, the shaft 70 is further configured to transmit a rotational force or movement onto the capsule 62.

The inner shaft assembly 54 can have various constructions appropriate for supporting a stented prosthetic heart valve within the capsule 62. In some embodiments, the inner shaft assembly 54 includes an inner support shaft 80, a tip 82, and the spindle 60. The inner support shaft 80 is sized to be slidably received within the lumen 76 of the delivery sheath assembly 52, and is configured for mounting of the release assembly 56. The inner support shaft 80 can include a distal segment 84 and a proximal segment 86. The distal segment 84 connects the tip 82 to the proximal segment 86, with the proximal segment 86, in turn, coupling the inner shaft assembly 54 to the handle 58. The components 80-86 can combine to define a continuous lumen 88 (referenced generally) sized to slidably receive an auxiliary component such as a guide wire (not shown).

The distal segment 84 can be a flexible polymer tube embedded with a metal braid. Other constructions are also acceptable so long as the distal segment 84 exhibits sufficient structural integrity to support a loaded, compressed stented prosthetic heart valve (not shown), as well as the release assembly 56. The proximal segment 86 can include, in some constructions, a leading portion 90 and a trailing portion 92. The leading portion 90 serves as a transition between the distal and proximal segments 84, 86, and thus in some embodiments is a flexible polymer tubing (e.g., PEEK) having an outer diameter slightly less than that of the distal segment 84. The trailing portion 92 has a more rigid construction (e.g., a metal hypotube), adapted for robust assembly with the handle 58. Other materials and constructions are also envisioned. For example, in alternative embodiments, the distal and proximal segments 84, 86 are integrally formed as a single, homogenous tube or solid shaft.

The tip 82 forms or defines a nose cone having a distally tapering outer surface adapted to promote atraumatic contact with bodily tissue. The tip 82 can be fixed or slidable relative to the inner support shaft 80.

The spindle 60 serves to selectively couple corresponding features of the stented prosthetic heart valve (not shown) relative to the inner shaft assembly 54 (e.g., relative to the inner support shaft 80), and can be configured for assembly over the inner support shaft 80. One embodiment of the spindle 60 is shown in greater detail in FIG. 4. In some constructions, the spindle 60 includes a tubular base 100, a hub 102, and a flange 104. The hub 102 and the flange 104 radially project from the tubular base 100, with the hub 102 forming various features configured to selectively engage the post(s) 40 (FIG. 2) of the stented prosthetic heart valve 20 (FIG. 1A) as described below.

The tubular base 100 is configured to facilitate mounting of the spindle 60 to the inner support shaft 80 (FIG. 3), and defines a central passageway or lumen (hidden in FIG. 4), an intermediate section 112, and a proximal section 114. The intermediate section 112 is formed or defined between the hub 102 and the flange 104, and the proximal section 114 is formed or defined proximal the flange 104. For reasons made clear below, the proximal section 114 forms a primary notch 116 and an optional secondary notch 118. The notches 116, 118 are configured to selectively receive a corresponding feature of the release assembly 56 (FIG. 3), and can assume various forms. For example, in some embodiments, the primary and secondary notches 116, 118 are each circumferential grooves. In other embodiments, one or both of the notches 116, 118 can extend less than an entirety of a circumference of the proximal section 114. Regardless, a longitudinal distal between the primary notch 116 and the hub 102 is selected as a function of a size of the release assembly 56. The secondary notch 118 is formed proximal the primary notch 116, and also has a longitudinal position relative to the hub 102 as a function of a size of the release assembly 56. These relationships are described in greater detail below.

The hub 102 radially projects from the tubular base 100, terminating at a rim 120. Further, the hub 102 forms or defines at least one longitudinal capture slot 122. In some embodiments, a plurality of the longitudinal capture slots 122 are formed in the hub 102, commensurate with the number of posts 40 (FIG. 1A) provided with the prosthetic heart valve 20 (FIG. 1A). In related embodiments, the plurality of capture slots 122 can be identical and are equidistantly spaced relative to a circumference of the hub 102. Alternatively, only a single one of the capture slots 122 need be provided. The capture slot(s) 122 extends through a thickness of the hub 102, and is open to a proximal face 124. A circumferential width of each of the capture slots 122 corresponds (e.g., is slightly greater than) with a circumferential width of the post shoulder 42 (FIG. 2). However, the circumferential width of each of the capture slots 122 at least at the proximal face 124 is less than the circumferential width of the post head 44 (FIG. 2).

The flange 104 is proximally spaced from the hub 102, and radially projects from the tubular base 100. With this spacing, then, the intermediate section 112 of the tubular base 100 provides a reduced diameter cylindrical surface interposed between the hub 102 and the flange 104. The larger diameter flange 104 combines with the larger diameter hub 102 and the intermediate section 112 to create a circumferential trough or groove 126 configured to selectively receive the post head 44 (FIG. 2) as described below. The capture slots 122 are open to the trough 126 at the proximal face 124, with the capture slots 122 and the trough 126 combining to define an engagement structure configured to selectively engage the post(s) 40 (FIG. 1A). The outer diameter of the flange 104 can approximate a maximum outer diameter of the hub 102 (e.g., the rim 120) for reasons made clear below. In other embodiments, however, the flange 104 can be omitted.

Returning to FIG. 3, the spindle 60 can be integrally formed as a homogenous part in some embodiments. The spindle 60 is constructed of a relatively rigid material able to maintain a structural integrity of the spindle 60 in supporting the prosthetic heart valve 20 (FIG. 1A) in the compressed arrangement. In other constructions, one or more of the hub 102 and the flange 104 can be separately manufactured and subsequently assembled to the tubular base 100. Alternatively, the hub 102 and/or the flange 104 can be directly mounted onto the inner support shaft 80. In yet other embodiments, the stent engagement features provided by the spindle 60 (e.g., one or both of the capture slots 122 and the trough 126) can be integrally formed by or into the inner support shaft 80. Further, other stent engagement structure configurations can alternatively be employed.

Figure 5A:
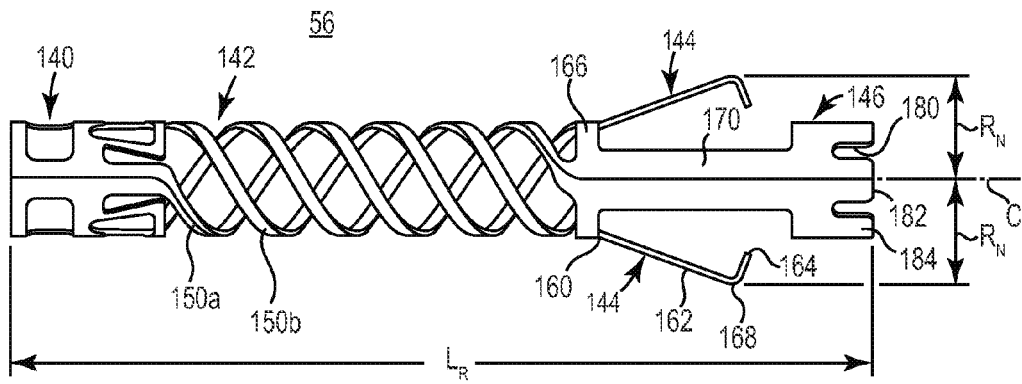
FIG. 5A is a side view of a release assembly component of the delivery device of FIG. 3, including a retraction member in a normal, relaxed condition and a release member in a normal, expanded condition.

The release assembly 56 is generally constructed to selectively capture the prosthetic heart valve 20 (FIG. 1A) to the spindle 60, and thus to the inner shaft assembly 54. One embodiment of the release assembly 56 is shown in FIG. 5A, and includes a base 140, a retraction member 142, at least one release member 144, and a retention member 146. In general terms, the base 140 associates the release assembly 56 with the inner support shaft 80 (FIG. 3). The retraction member 142 longitudinally arranges the retention member 146 relative to the base 140. In this regard, the retraction member 142 is self-retractable from an extended condition to a relaxed, retracted condition, with the release member 144 configured to temporarily retain the retraction member 142 in the extended condition. The retention member 146 is sized to be slidably disposed over the spindle 60 when so positioned by an arrangement of the release assembly 56.

The base 140 can assume various configurations appropriate for non-moveable, affixed mounting to (or relative to) the inner support shaft 80 (FIG. 3). For example, the base 140 can be a collar or ring that is bonded to the inner support shaft 80. Other structures appropriate for establishing a fixed location relative to the inner support shaft 80, as well as resisting forces generated in or by the retention member 142 are also envisioned. For example, in other embodiments, the base 140 can be omitted and a proximal end of the retraction member 142 opposite the retention member 146 directly attached to the inner support shaft 80. Alternatively, the base 140 and/or the retraction member 142 can be affixed to the proximal section 114 (FIG. 4) of the spindle 60 (FIG. 4) that in turn is attached to the inner support shaft 80.

Figure 5B:
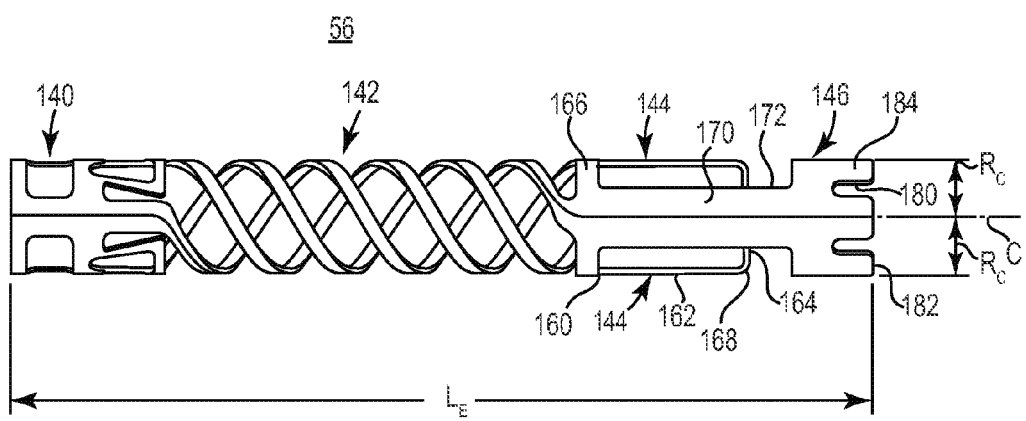
FIG. 5B is a side view of the release assembly of FIG. 5A, including the retraction member forced to an extended condition, and the release member forced to compressed condition.

The retraction member 142 is a linear spring-like body, adapted to self-transition or self-retract in longitudinal length from an extended condition (FIG. 5B) to the normal (or relaxed), retracted condition reflected in FIG. 5A. In some embodiments, the retraction member 142 is a tubular body (e.g., a metal tube) laser cut to define helical spring segments 150a, 150b. With this construction, the retraction member 142 has a shape memory set to the relaxed or retracted condition of FIG. 5A, with the condition of the retraction member 142 dictating an overall longitudinal length of the release assembly 56 (e.g., longitudinal distance between a proximal end of the base 140 and a distal end of the retention member 146). The linear spring-like construction permits longitudinal extension of the retraction member 142, and thus of the retention member 146 relative to the base 140. For example, the normal, relaxed condition of the retraction member 142 establishes a normal or retracted length $L_R$ for the release assembly 56 as identified in FIG. 5A. When the retraction member 146 is subjected to an external, longitudinally expansive force, the retraction member 146 elastically extends to the extended condition, resulting in the release assembly 56 assuming an extended length $L_E$ (FIG. 5B). The extended length $L_E$ is greater than the relaxed or normal length $L_R$. Upon removal of the external, longitudinally-expansive force, the retraction member 142 self-transitions or self-retracts back to the relaxed or retracted condition (and thus the release assembly 56 reverts back to the relaxed length $L_R$). Further, the retention member 142 is configured such that an outer diameter defined by the retraction member 142 is substantially the same in the relaxed condition and the extended condition. That is to say, the retraction member 142 does not overtly change in outer diameter when transitioning between the relaxed, retracted condition and the extended condition. Alternatively, the outer diameter may experience some change between the relaxed and extended conditions. Regardless, the outer diameter of the retraction member 142 in each of the relaxed, retracted condition and the extended condition is less than an inner diameter of the lumen 76 (FIG. 3) of the delivery sheath assembly 52 (FIG. 3).

Figure 5C:
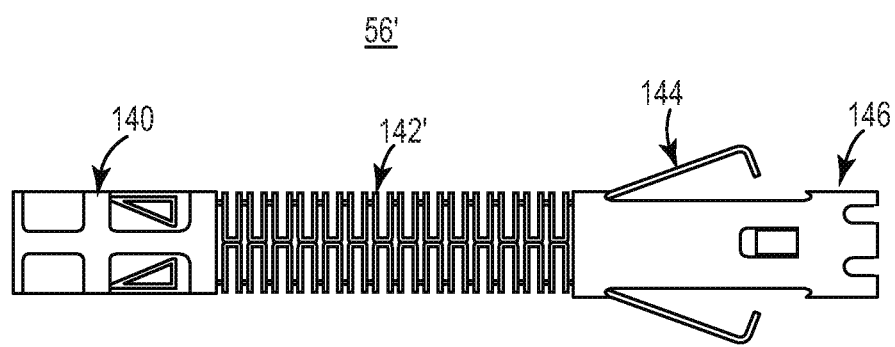
FIG. 5C is a side view of an alternative release assembly useful with the delivery device of FIG. 3.

The retraction member 142 can incorporate various other constructions that facilitate longitudinal self-retraction from an extended condition to a relaxed, retracted condition. For example, FIG. 5C illustrates an alternative release assembly 56' including a retraction member 142' in the form of a laser cut tube with a spring segment arrangement differing from that of FIG. 5A.

Returning to FIGS. 5A and 5B, the release member 144 extends distal the retraction member 142, and in some constructions is a leaf spring-like or deflectable arm. As shown in FIGS. 5A and 5B, two of the release members 144 are provided with the release assembly 56 in some constructions; alternatively, one or more than two of the release members 144 can be included. Regardless, the release member 144 has a normal, expanded condition (FIG. 5A) and can be directed to a radially compressed condition as shown in FIG. 5B by an external force (e.g., when disposed within an outer sheath or catheter). Upon removal of the external radially compressive force, the release member 144 self-expands back toward the normal, expanded condition. Relative to a central axis C of the release assembly 56, a maximum radial projection $R_N$ (FIG. 5A) of the release member 144 in the normal, expanded condition is greater than a maximum radial projection $R_C$ (FIG. 5B) in the compressed condition. For reasons made clear below, the normal condition maximum radial projection $R_N$ is greater than a radius of the delivery sheath lumen 76 (FIG. 3); conversely, the compressed condition maximum radial projection $R_C$ is less than the radius of the delivery sheath lumen 76.

With embodiments in which the release member 144 is a deflectable arm, the release member arm 144 defines a fixed end 160, an intermediate portion 162, and a free end 164. The fixed end 160 is spatially affixed relative to the retraction member 142, for example via a ring or similar body 166 defined by the release assembly 56 distal the retention member 142. Where a plurality of the release member arms 144 are included, the corresponding fixed ends 160 are commonly connected to the ring 166. The intermediate portion 162 projects distally from the fixed end 160, and is formed to have a memory set shape biased radially outwardly from the central axis C. In some constructions, the intermediate portion 162 defines an angled segment 168. As shown in the normal condition of FIG. 5A, the intermediate portion 162 projects generally radially outwardly in extension from the fixed end 160 to the angled segment 168; conversely, the angled segment 168 defines a generally radially inward projection to the free end 164. Thus, the release member arm 144 can have an L-like shape, although other shapes for the angled segment 168 are also envisioned that may or may not be curved. With the one construction of FIG. 5A, however, in the normal, expanded condition, the free end 164 is spaced radially outwardly from a circumference of the retention member 146. Stated otherwise, a radial distance between the central axis C and the free end 164 in the normal, expanded condition is less than a radius of the retention member 146. Conversely, and as best shown in FIG. 5B, in the compressed condition, the free end 164 is radially spaced form the central axis C by a distance that is less than a radius of the retention member 146.

In some embodiments, the retraction member 142 is connected to the retention member 146 by the ring 166 and a connection body 170. The connection body 170, in turn, forms a clearance slot 172 that is radially aligned with the free end 164 of the release member deflection arm 144. Thus, the clearance slot 172 permits forced transitioning of the release member 144 to the compressed arrangement, with the free end 164 passing through the clearance slot 172. Where two (or more) of the release member arms 144 are provided, the connection body 170 forms a corresponding number of the clearance slots 172.

Figure 4:
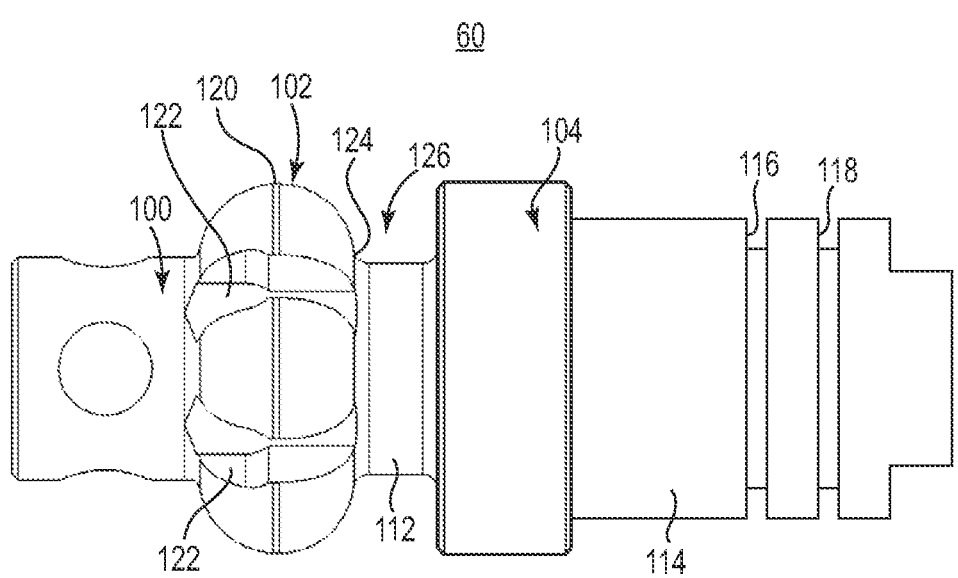
FIG. 4 is an enlarged, side view of a spindle portion of the delivery device of FIG. 3.

The retention member 146 is a sleeve-like body sized to be slidably received over the spindle 60 (FIG. 4). In this regard, the retention member 146 is designed to move freely over the flange 104 (FIG. 4) due to a gap clearance (e.g., on the order 0.01 inch or greater) that is provided between the retention member 146 and the maximum outer diameter of the flange 104. In some constructions, the retention member 146 forms or defines at least one longitudinal notch 180 extending from, and open relative to, a distal end 182 thereof. The retention member 146 normally includes a plurality of the notches 180 corresponding with a number of the capture slots 122 (FIG. 4) provided with the hub 102. With embodiments in which the retention member 146 forms two or more of the notches 180, two (or more) fingers 184 are formed by or between adjacent ones of the notches 180. In other embodiments, the notches 180 can be omitted.

The release assembly 56 can be made of one or more materials such as metals or polymers (e.g., Nitinol®, stainless steel, Delrin®, and the like). The material(s) has a thickness on the order of 0.002-0.007 inch, for example, although the thickness can be lower or higher than this size range. In some constructions, the release assembly 56 is integrally formed from a single metal tube that is laser cut to define the various features described above. In other embodiments, one or more of the components 140-146 can be separately formed and subsequently assembled.

Figure 6A:
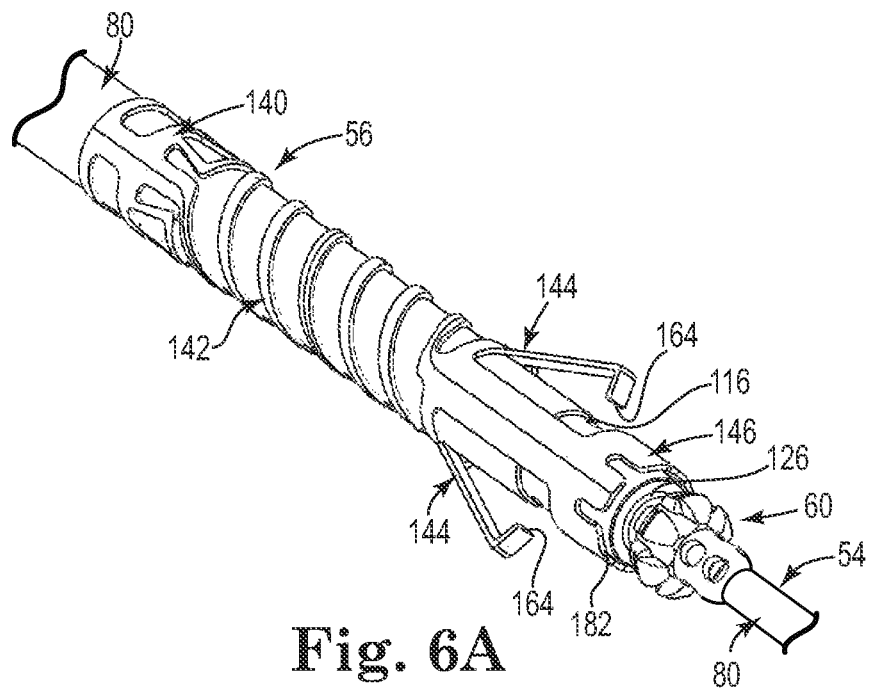
FIG. 6A is a perspective view of the release assembly of FIG. 5A assembled to an inner shaft assembly component of the delivery device of FIG. 3, including the retraction member in the normal, relaxed condition and the release member in the normal, expanded condition.
Figure 6B:
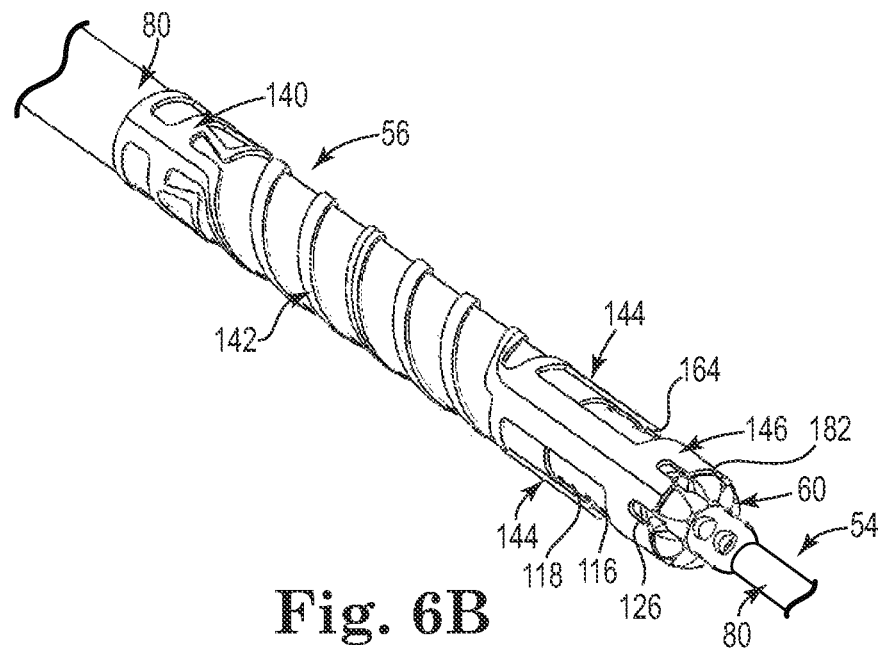
FIG. 6B is a perspective view of the components of FIG. 6A, including the retraction member in the extended condition and the release member in the compressed condition.

Assembly of the release assembly 56 to the inner shaft assembly 54 (including the spindle 60) is shown in FIGS. 6A and 6B. The release assembly 56 is mounted to (e.g., over) the inner support shaft 80, as is the spindle 60. Alternatively, the release assembly 56 can incorporate an inner tube to which the base 140 is attached (and over which the retraction member 142 is slidably received), with the inner tube being assembled to the inner support shaft 80 (or between separate, proximal and distal portions of the inner support shaft 80). Regardless, the base 140 is spatially affixed relative to the inner support shaft 80 at a predetermined location relative to the trough 126 of the spindle 60. For example, relative to the normal, relaxed condition of the retraction member 142 (FIG. 6A), the mounting body 140 is positioned such that the retention member 146 (and in particular the distal end 182 thereof) is proximal or proximally spaced from the trough 126. Conversely, in the extended condition of the retraction member 142 (FIG. 6B), the retention member 146 is located such that the distal end 182 is distal the trough 126 (partially hidden in FIG. 6B). The release member(s) 144 serves to retain the retraction member 142 in the extended condition of FIG. 6B by being exteriorly compressed into the compressed condition in which the corresponding free end 164 (partially hidden in FIG. 6B, but fully shown in FIG. 6A) is nested into engagement with the primary notch 116 (referenced generally). Thus, a longitudinal distance between the distal end 182 of the retention member 146 and the free end 164 of the release member 144 corresponds with (e.g., is slightly greater than) the longitudinal distance between the primary notch 116 and the trough 126 so as to ensure that when the free end 164 is nested within the primary notch 116, the retention member 146 is coaxially over the trough 126. Conversely, when the release member 144 is permitted to self-expand to the normal, expanded condition of FIG. 6A and release from the spindle 60, the retraction member 142 is allowed to self-transition or retract back to the relaxed condition, thereby retracting the retention member 146 from the hub 102 and the trough 126. In effect, the release member 144 serves as a latch. It will be understood that by affixing the base 140 relative to the inner support shaft 80, the base 140 remains stationary while the retention member 146 moves proximally with self-retraction of the retraction member 142 from the extended condition (FIG. 6B) to the relaxed condition (FIG. 6A). In some embodiments, with the retraction member 142 in the relaxed condition, the free end 164 of the release member(s) 144 is radially aligned with the optional secondary notch 118 (referenced generally in FIG. 6B). When the release member(s) 144 is forced back to the compressed arrangement of FIG. 6B (and the retraction member 142 remains in the relaxed condition), then, the free end 164 can nest within the secondary notch 118.

Returning to FIG. 3, the handle 58 generally includes a housing 200 and an actuator mechanism 202 (referenced generally). The housing 200 maintains the actuator mechanism 202, with the actuator mechanism 202 configured to facilitate sliding movement of the delivery sheath assembly 52 relative to the inner shaft assembly 54 and the release assembly 56. The housing 200 can have any shape or size appropriate for convenient handling by a user. In one simplified construction, the actuator mechanism 202 includes a user interface or actuator 204 slidably retained by the housing 200 and coupled to a sheath connector body 206. The proximal end 72 of the delivery sheath assembly 52 is coupled to the sheath connector body 206 (e.g., via an optional mounting boss 208 in some embodiments). The inner shaft assembly 54, and in particular the proximal tube 86, is slidably received within a passage 210 of the sheath connector body 206, and is rigidly coupled to the housing 200. Sliding of the actuator 204 relative to the housing 200 thus causes the delivery sheath assembly 52 to move or slide relative to the inner shaft assembly 54 and the release assembly 56, for example to effectuate deployment of a prosthesis (not shown) from the inner shaft assembly 54 as described below. Alternatively, the actuator mechanism 202 can assume a variety of other forms differing from those implicated by the illustration of FIG. 3. Similarly, the handle 58 can incorporate other features, such as a cap 212 and/or a fluid port assembly 214.

FIGS. 7A and 7B illustrate, in simplified form, a portion of a system 250 in accordance with the present disclosure for restoring (including replacing) a defective heart valve of a patient and including the stented prosthetic heart valve 20 loaded within the delivery device 50. For ease of illustration, only a portion of the prosthetic heart valve 20 is shown in FIG. 7B (in particular, a portion of the stent frame 22). In the delivery state of the delivery device 50 in FIGS. 7A and 7B, the prosthetic heart valve 20 is crimped over the inner shaft assembly 54, with the delivery sheath assembly 52 located such that the capsule 62 surrounds and compressively retains the prosthetic heart valve 20 in the compressed arrangement shown, thereby defining a loaded mode of the system 250. Further, the release assembly 56 (a distal-most segment of which is shown in FIG. 7A) is arranged such that the retention member 146 is disposed over the spindle 60, and in particular over least the trough 126 (referenced generally). The stent posts 40 (one of which is shown in FIG. 7B) are engaged with the spindle 60, including the head 44 (hidden in FIG. 7B) disposed within the trough 126 (hidden in FIG. 7B), and the shoulder 42 disposed within one of the capture slots 122. The retention member 146 is disposed over the spindle 60 to retain the posts 40 within the corresponding capture slots 122 and the trough 126. The retention member 146 position of FIG. 7B includes the retraction member 142 being forced to the extended condition. The release member(s) 144 holds the retraction member 142 in the extended condition and prevents self-retraction by being forced to the compressed condition shown in which the release member(s) 144 is deflected radially inwardly such that the free end 164 nests within the primary notch 116. More particularly, the inner diameter of the delivery sheath assembly 52 (shown in cross-section in FIG. 7B) is less than the normal, maximum radial projection $R_N$ (FIG. 5A) of the release member(s) 144. Thus, when inserted within the delivery sheath assembly lumen 76, the delivery sheath assembly 52 forces the release member(s) 144 to the compressed condition (it being understood that a small gap is shown in FIG. 7B between the release members 144 and the inner diameter of the delivery sheath assembly 52 for ease of explanation). The nested arrangement of the free end 164 to the spindle 60 effectively locks or holds the release assembly 56 in the arrangement shown, with the delivery sheath assembly 52 resisting or preventing self-expansion of the release member(s) 144.

The loaded system 250 can then be used to percutaneously deliver the prosthetic heart valve 20 to an implantation site, such as a defective heart valve. For example, the delivery device 50 is manipulated to advance the compressed prosthetic heart valve 20 toward the implantation site in a retrograde manner through a cut-down to the femoral artery, into the patient's descending aorta, over the aortic arch, through the ascending aorta, and approximately midway across the defective aortic valve (for an aortic replacement procedure). The prosthetic heart valve 20 can then be partially or fully deployed from the delivery device 50. With either procedure, the capsule 62 is proximally retracted or withdrawn (via operation of the handle 58 (FIG. 3)) from over the prosthetic heart valve 20. As generally reflected in FIGS. 8A and 8B, proximal retraction of the capsule 62 continues until the distal end 74 is immediately distal the hub 102. For ease of illustration, only a portion of the prosthetic heart valve 20 is shown in FIG. 8B (in particular, one of the stent posts 40). Because the release member(s) 144 is still within the capsule 62 in the arrangement of FIGS. 8A and 8B, the retention member 146 remains in the distally forward position relative to the hub 102 via "locked" relationship of the release member(s) 144 to the spindle 60, thus the retraction member 142 remains in the extended condition. As a point of reference, an internal diameter of the delivery sheath 52 may vary along a length thereof (e.g., transition from the shaft 70 to the capsule 62, along the capsule 62, etc.). In some embodiments, the release member(s) 144 are sized and shaped to maintain the locked relationship while "moving" through the small changes in the delivery sheath internal diameter (e.g., a length of the release member 144 between the angled segment 168 and the free end 164 is sufficiently sized so that even if the release member 144 slightly deflects radially outwardly in the presence of a slightly larger internal diameter section of the delivery sheath 52, the fixed end 164 remains engaged with the spindle 60). As shown in simplified form in FIG. 8A, partial retraction of the capsule 62 allows self-expansion of an exposed distal region 260 of the prosthetic heart valve 20 relative to the distal end 74 of the capsule 62 to occur.

So long as the distal end 74 of the capsule 62 remains distal the release member(s) 144, the release member(s) 144 remains in the compressed or deflected condition (and the retraction member 142 in the extended condition) such that the retention member 146 remains over the trough 126 (referenced generally in FIG. 8B). Thus, the head 44 (hidden in FIG. 8B) of each of the posts 40 remains engaged within the trough 126. As a result, in the stage of the partial deployment mode of FIGS. 8A and 8B, the prosthetic heart valve 20 is able to partially expand or deploy, yet remains coupled to the delivery device 50 via the release assembly 56 and the spindle 60.

Figure 8C:
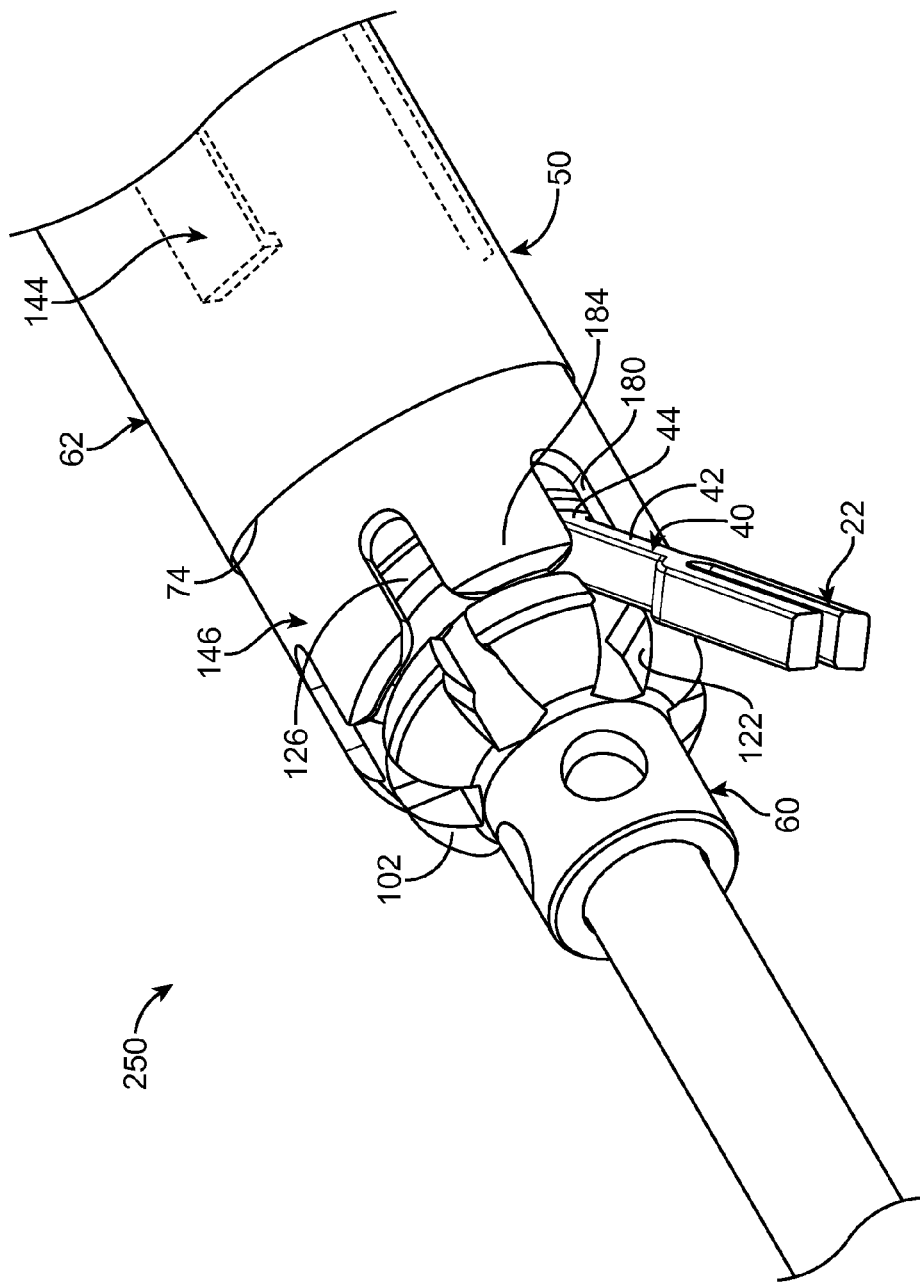
FIG. 8C is an enlarged, perspective view of the system of FIG. 7A in a further stage of partial deployment.

Partial deployment of the prosthetic heart valve 20 can also include further sequential retraction of the capsule 62 from the position of FIGS. 8A and 8B. For example, in the partial deployment stage reflected in FIG. 8C, the distal end 74 of the capsule 62 (shown in phantom in FIG. 8C) is further retracted relative to the hub 102 (as compared to the stage of FIG. 8A), with the distal end 74 located proximal the notches 180 and distal the release member(s) 144. Because the release member(s) 144 is still within, and thus acted upon by, the capsule 62, the retraction member 142 (FIG. 8B) remains extended and the retention member 146 remains over the trough 126 such that the stent frame 22 is coupled between the retention member 146 and the spindle 60. With embodiments in which the retention member 146 forms the notches 180, FIG. 8C further reflects that in this stage of the partial deployment mode, the stent frame posts 40 can pivot relative to the spindle 60. For example, with the distal end 74 of the capsule 62 proximal the notch 180 identified in FIG. 8C, the self-expanding attribute of the stent frame 22 causes the shoulder 42 of the post 40 to slide through the corresponding capture slot 122 and the corresponding notch 180, with the head 44 effectively pivoting within the trough 126. Even with this pivoting movement, however, the head 44 remains captured within the trough 126 via the fingers 184.

In the stage of partial deployment of FIG. 8C (or in any other sequentially prior stage of partial deployment), the clinician can perform desired evaluations of the partially deployed prosthetic heart valve 20 (FIG. 8A) relative to the implantation site. Notably, a substantial majority of the prosthetic heart valve 20 is in an expanded arrangement, including, for example, the inflow region 30 (FIG. 1A) and at least a portion of the outflow region 32 (FIG. 1A). Thus, the systems, delivery devices, and methods of the present disclosure afford the clinician the ability to make an accurate estimate of the position of the prosthetic heart valve 20 relative to the implantation site. Under circumstances where the clinician determines that the prosthetic heart valve 20 should be repositioned, the capsule 62 can, in some constructions, be distally advanced back over the prosthetic heart valve 20, thereby resheathing or recapturing the prosthetic heart valve 20 and returning it to the compressed arrangement. Alternatively, the delivery device 50 can incorporate other features to effectuate recapturing of the prosthetic heart valve 20.

When full deployment of the prosthetic heart valve 20 from the delivery device 50 is desired, the capsule 62 is further proximally retracted relative to the release member(s) 144. As shown in FIG. 9A, as the distal end 74 of the delivery sheath assembly 52 is moved or withdrawn proximal the release member(s) 144, the release member(s) 144 is released from the confines of the delivery sheath assembly 52. As a result, the release member(s) 144 self-expands toward the natural, expanded state, with the free end 164 thus withdrawing from the primary notch 116. Effectively, then, the release member(s) 144 "senses" full retraction of the delivery sheath assembly 52. Once the release member(s) 144 has released from engagement with the spindle 60 (or other component of the inner shaft assembly 54 to which the free end 164 was temporarily engaged), the longitudinally expansive force imparted upon the retraction member 142 is removed, thereby allowing the retraction member 142 to immediately self-retract to or toward the relaxed, retracted state of FIG. 9B. This movement, in turn, proximally retracts the retention member 146 from the hub 102 and the trough 126 as reflected by a comparison of the arrangement of FIG. 9A with that of FIG. 9B (it being understood that the delivery sheath assembly 52 has been further proximally retracted in the view of FIG. 9B from the arrangement of FIG. 9A). Retraction of the retention member 146 from the hub 102 and the trough 126 permits the stent posts 40 (one of which is shown in FIGS. 9A and 9B) to fully release from the inner shaft assembly 54/spindle 60 due, for example, to self-expansion of the prosthetic heart valve stent frame 22. Thus, with release assemblies of the present disclosure, the retraction/release operation is separated from the delivery sheath position "sensing" operation via the separate retraction member 142 and release member 144.

Figure 9C:
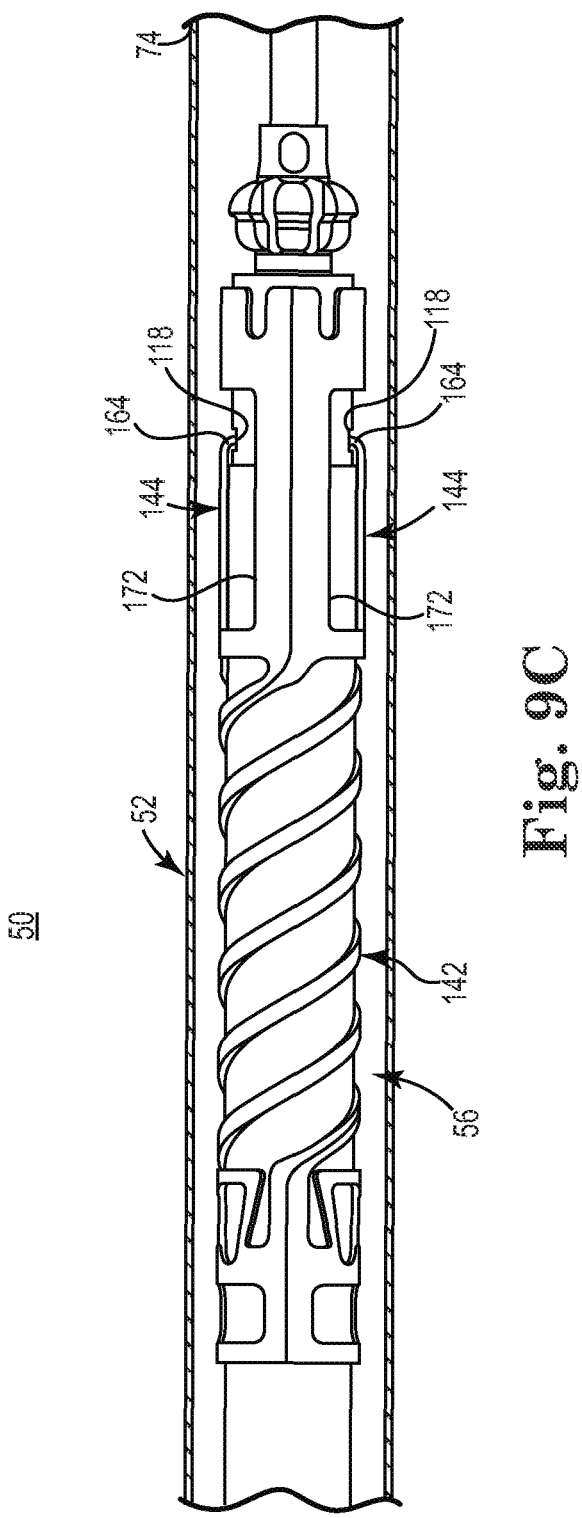
FIG. 9C is an enlarged, side view of the delivery device of FIG. 3 in a removal state.

Following release/deployment of the prosthetic heart valve 20, the delivery device 50 can be percutaneously withdrawn from the patient. To facilitate removal, the delivery device 50 can be transitioned to a removal state as shown in FIG. 9C. It will be recalled that in the sequentially previous deployment state, the retraction device 142 has self-retracted to the relaxed, retracted state. As shown in FIG. 9C, the delivery sheath assembly 52 is subsequently distally advanced such that the distal end 74 is now distal the release member(s) 144. This action, in turn, forces the release member(s) 144 back to the compressed arrangement, with the free end(s) 164 passing through the corresponding clearance slot 172 and nesting within the optional secondary notch 118, thereby returning the release assembly 56 to a low profile conducive to easy withdrawal from the patient. In other embodiments, the secondary notch 118 can be omitted.

The delivery devices of the present disclosure provide percutaneous placement of a stented prosthetic heart valve for replacement of an aortic valve, for example. Alternatively, the systems and devices can be used for replacement or repair of other valves and/or in other portions of the body in which a stent is to be implanted. When delivering a valved stent to replace an aortic valve, the delivery devices of the present disclosure can be used with a retrograde delivery approach, for example, although it is contemplated that an antegrade delivery approach can be used, with certain modifications to the delivery device. With the systems described herein, full or partial blood flow through the native valve can advantageously be maintained during a period when the valved stent is being deployed into the patient, but is not yet released from its delivery device. This feature can help to prevent complications that may occur when blood flow is stopped or blocked during valve implantation with some other known delivery devices. In addition, it is possible for the clinician to thereby evaluate the opening and closing of leaflets, examine for any paravalvular leakage, and evaluate coronary flow and proper positioning of the prosthetic heart valve within the target anatomy before final release of the stented prosthesis.

The delivery devices shown and described herein can be modified for delivery of balloon-expandable stented prosthetic heart valves, within the scope of the present disclosure. That is to say, delivering balloon-expandable stents to an implantation location can be performed percutaneously using modified versions of the delivery devices of the present disclosure. In general terms, this includes providing a transcatheter assembly that can include a delivery sheath and/or additional sheaths as described above. The devices will further include a delivery catheter, a balloon catheter, and/or a guide wire. A delivery catheter used in this type of delivery device defines a lumen within which the balloon catheter is received. The balloon catheter, in turn, defines a lumen within which the guide wire is slidably disposed. Further, the balloon catheter includes a balloon that is fluidly connected to an inflation source. With the stented valve mounted to the balloon, the transcatheter assembly is delivered through a percutaneous opening in the patient via the delivery device. Once the stented prosthetic heart valve is properly positioned, the balloon catheter is operated to inflate the balloon, thus transitioning the stented prosthesis to an expanded arrangement.

The systems, devices, and methods of the present disclosure provide a marked improvement over previous designs. The delivery device is configured so that the stent frame of the stented prosthetic heart valve will release from the delivery device at a pre-designated step of the delivery sequence. These delivery devices thereby advantageously allow the clinician to entirely remove an outer sheath from a valved stent prior to releasing the stent from the delivery device. In addition, the systems of the present disclosure allow the inflow region and at least a portion of the outflow region of the valved stent to open or release so that the valve structure function can be determined prior to final release of the stented valve. The disclosed release assembly provides a simplified design that better ensures consistent triggering or deployment, and minimizes opportunities for malfunctions (e.g., jams) by separating the outer delivery sheath sensing and retention member retraction functions.

Although the present disclosure has been described with reference to preferred embodiments, workers skilled in the art will recognize that changes can be made in form and detail without departing from the spirit and scope of the present disclosure.

What is claimed is:

1. A delivery device for percutaneously deploying a stented prosthetic heart valve including a stent frame to which a valve structure is attached, the device comprising:
   a delivery sheath terminating at a distal end and defining a lumen;
   an inner shaft assembly slidably disposed within the lumen and including an engagement structure configured to selectively engage a prosthetic heart valve; and
   a release assembly disposed between the delivery sheath and the inner shaft assembly, the release assembly defining a central axis and including:
   a base coupled to the inner shaft assembly proximal the engagement structure,
   a retraction member distal the base and configured to self-retract in longitudinal length from an extended condition to a relaxed, retracted condition,
   a release member distal the retraction member and configured to self-expand in radial projection relative to the central axis from a compressed condition to a normal, expanded condition,
   a retention member distal the release member;
   wherein the device is configured to provide:
   a delivery state in which the distal end is distal the retention member, the release member is in the compressed condition, and the retraction member is in the extended condition,
   a deployment state in which the distal end is proximal the release member, the release member is in the normal, expanded condition, and the retraction member is in the relaxed, retracted condition.

2. The delivery device of claim 1, wherein the engagement structure includes a spindle forming a plurality of longitudinal capture slots and a circumferential trough.

3. The delivery device of claim 2, wherein the delivery state includes the retention member being disposed over the circumferential trough.

4. The delivery device of claim 2, wherein the deployment state includes the retention member located proximal the circumferential trough.

5. The delivery device of claim 1, wherein a longitudinal distance between the base and the retention member in the extended condition of the retraction member is less than a longitudinal distance between the base and the retention member in the relaxed, retracted condition.

6. The delivery device of claim 1, wherein the retention member is a linear spring.

7. The delivery device of claim 6, wherein the linear spring is formed by a laser cut metal tube.

8. The delivery device of claim 1, wherein the release member is a deflection arm having a fixed end, a free end, and an intermediate portion having a memory set angled shape.

9. The delivery device of claim 8, wherein the fixed end is spatially affixed to the retraction member and the free end is radially deflectable relative to the central axis, with the arm pivoting at the fixed end.

10. The delivery device of claim 9, wherein the release assembly further includes a connection body interconnecting a distal side of the retraction member with a proximal side of the retention member, the connection body forming a clearance slot sized and positioned to permit passage of the free end in transitioning from the expanded condition to the compressed condition.

11. The delivery device of claim 10, wherein the compressed condition includes the free end projecting through the clearance slot.

12. The delivery device of claim 11, wherein the inner shaft assembly further includes a tubular base forming a primary notch proximal the engagement structure, and further wherein the delivery state includes the free end nested within the primary notch.

13. The delivery device of claim 12, wherein the tubular base further forms a secondary notch proximal the primary notch, and further wherein the delivery device is configured to provide a removal state in which the distal end of the delivery sheath is distal the release member, the retention member is in the relaxed, retracted condition, and the deflection arm is in the compressed condition including the free end nested within the secondary notch.

14. The delivery device of claim 8, wherein the release member deflection arm is a first release member deflection arm, and further wherein the release assembly further includes a second release member deflection arm circumferentially opposite the first release member deflection arm.

15. The delivery device of claim 1, wherein the release member defines a maximum radial projection relative to the central axis in the normal, expanded condition, and further wherein the maximum radial projection is greater than a radius of the delivery sheath lumen.

16. A system for restoring a defective heart valve of a patient, the system comprising:
    a prosthetic heart valve having a stent frame and a valve structure attached to the stent frame, the stent frame defining a distal region and a proximal region, the proximal region forming at least one post; and
    a delivery device comprising:
    a delivery sheath terminating at a distal end and defining a lumen, an inner shaft assembly slidably disposed within the lumen and including an engagement structure,
    a release assembly for selectively coupling the prosthetic heart valve relative to the inner shaft assembly, the release assembly defining a central axis and including:
    a base coupled to the inner shaft assembly proximal the engagement structure,
    a retraction member distal the base and configured to self-retract in longitudinal length from an extended condition to a relaxed, retracted condition,
    a release member distal the retraction member and configured to self-expand in radial projection relative to the central axis from a compressed condition to a normal, expanded condition,
    a retention member distal the release member;
    wherein the system is configured to provide a loaded mode in which the prosthetic heart valve is retained within the delivery sheath and to the inner shaft assembly, including the at least one post slidably captured to the engagement structure by the retention member, with the retraction member in the extended condition and the release member in the compressed condition.

17. The system of claim 16, wherein the system is further configured to provide a deployment mode in which the distal end is proximal the release member, the release member is in the normal, expanded condition, and the retraction member is in the relaxed, retracted condition to withdraw the retention member from over the post and permit the prosthetic heart valve to self-deploy from the delivery device.

18. The system of claim 16, wherein the engagement structure includes a spindle forming a plurality of longitudinal capture slots and a circumferential trough, and further wherein the loaded mode includes the post slidably disposed within one of the capture slots and the trough, the retention member extending distal the trough.

19. The system of claim 16, wherein the retention member is a linear spring.

20. The system of claim 16, wherein the release member is a deflection arm having a fixed end, a free end, and an intermediate portion having a memory set angled shape.

21. The system of claim 20, wherein the fixed end is spatially affixed to the retraction member and the free end is radially deflectable relative to the central axis, pivoting at the fixed end.

22. The system of claim 21, wherein the release assembly further includes a connection body interconnecting a distal side of the retraction member with a proximal side of the retention member, the connection body forming a clearance slot sized and positioned to permit passage of the free end.

23. The system of claim 22, wherein the compressed condition includes the free end projecting through the clearance slot.

24. The system of claim 23, wherein the inner shaft assembly further includes a tubular base forming a primary notch proximal the engagement structure, and further wherein the delivery state includes the free end nested within the primary notch.

25. The system of claim 16, wherein the delivery mode includes the delivery sheath forcing the release member to the compressed condition.

26. The system of claim 16, wherein the delivery device is further transitionable from the deployment mode to a removal state following deployment of the prosthetic heart valve, the removal state including the distal end of the delivery sheath being distal the release member to force the release member to the compressed condition and the retraction member in the relaxed, retracted condition.

* * * * *